United States Patent [19]

Owen

[11] 3,930,976
[45] Jan. 6, 1976

[54] GLASS ELECTRODE ASSEMBLY
[75] Inventor: John Cadwaladr Owen, Lightwater, England
[73] Assignee: George Kent Limited, Luton, England
[22] Filed: Jan. 31, 1974
[21] Appl. No.: 438,399

Related U.S. Application Data
[63] Continuation-in-part of Ser. No. 164,410, July 20, 1971, abandoned.

[52] U.S. Cl............ 204/195 G; 204/286; 204/297 R
[51] Int. Cl.² .......................................... G01N 27/36
[58] Field of Search ............ 204/1 T, 195 G, 195 R

[56] References Cited
UNITED STATES PATENTS

| | | | |
|---|---|---|---|
| 2,256,733 | 9/1941 | Cary et al. ...................... | 204/195 G |
| 2,756,203 | 7/1956 | Gilbert............................ | 204/195 G |
| 2,844,532 | 7/1958 | White et al. .................... | 204/195 G |
| 3,234,117 | 2/1966 | Rost et al........................ | 204/195 R |
| 3,424,664 | 1/1969 | Severinghaus.................. | 204/195 G |
| 3,476,671 | 11/1969 | Petty............................... | 204/195 R |
| 3,551,315 | 12/1970 | Friconneau et al............. | 204/195 G |

FOREIGN PATENTS OR APPLICATIONS

| | | | |
|---|---|---|---|
| 667,471 | 3/1952 | United Kingdom............. | 204/195 G |

*Primary Examiner*—T. Tung
*Attorney, Agent, or Firm*—Brisebois & Kruger

[57] ABSTRACT

An electrochemical glass electrode comprising a glass membrane sealing an end of a glass tube, a quantity of electrolyte in the tube and in contact with the internal surface of the membrane, a conductor extending through a rubber plug in the tube and immersed at one end in the electrolyte, and a screened electrical lead extending into the tube and connected to the other end of the conductor. The rubber plug is a sealing fit in the tube and provides an electrically insulating barrier between the electrolyte and the screen on the electrical lead.

3 Claims, 3 Drawing Figures

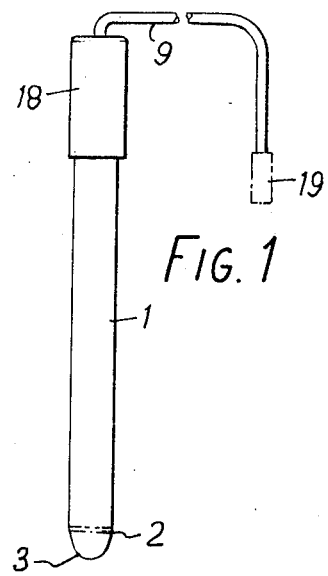
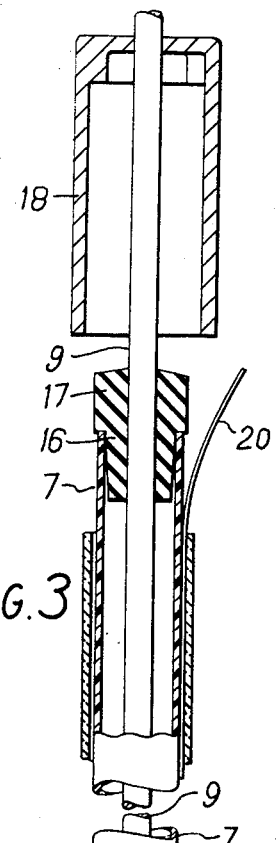
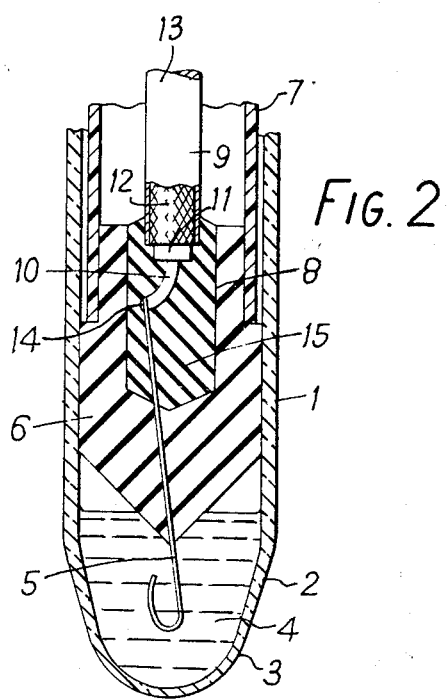
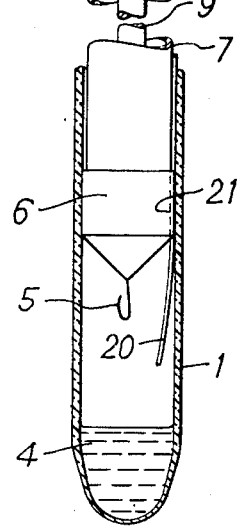

GLASS ELECTRODE ASSEMBLY

This application is a Continuation-in-Part of my copending application, Ser. No. 164,410, filed July 20, 1971, now abandoned.

This invention relates to electrode assemblies for use in electro-chemical test or measurement, and is concerned more particularly with glass electrode assemblies of the kind in which the electrical conductor in contact with the electrolyte is connected to the output terminal through a screened electrical lead.

In the past glass electrode assemblies using screened electrical leads comprise inner and outer glass tubes which co-operate to provide an annular chamber for the screening, the glass member providing the membrane of the electrode being sealed to an exposed end of the inner tube, one end of the outer tube being sealed to the inner tube in the region adjacent the exposed end thereof, and the conductor being sealed in the opposite end of the inner tube and in contact with the electrolyte in the inner tube. These glass electrode assemblies were difficult to manufacture. In particular it was difficult to anneal the glass in the sealing regions, giving rise to inherent mechanical stress in the glass. The only ways possible of fastening the lead to the conductor resulted in a large volume for the electrode space and the danger of unsatisfactory operation if the assembly was not in a substantially upright position.

One object of the present invention is to provide a glass electrode assembly having a screened electrical lead which involves less elaborate glass working and a much simpler and more effective screening arrangement than in the prior known electrode assemblies. A further object of the invention is to provide an electrode assembly in which the electrolyte space can be small and can be substantially filled with electrolyte, with a corresponding improvement in performance over the prior known electrode assemblies.

According to the present invention there is provided an electrochemical electrode assembly comprising a tube of glass terminating in a glass member defining a glass membrane, said member containing a quantity of electrolyte liquid in contact with the internal surface of said membrane, the external surface of said membrane being externally accessible, closure means retaining the electrolyte in said tube, an electrical conductor passing through said closure means and extending into said electrolyte, an electrical lead extending into said tube and connected to said conductor, and an electrical screen surrounding said lead and extending to the proximity of said closure means, said closure means being made of a resilient electrically-insulating material and being of a size such that it is compressed by said tube and provides a sealing fit against the inside wall of the tube and the electrical conductor so as to form an electrically insulating barrier between the electrolyte and said electrical screen.

The electrode assembly of the invention may be manufactured by providing a glass tube having a substantially cylindrical portion terminating in a glass member providing a glass membrane, inserting electrolyte in said member, providing a closure plug of resilient electrically-insulating material of a size adapted to be a sealing fit within said cylindrical portion to retain said electrolyte in said member, said closure plug having an electrical conductor embedded in and passing therethrough, providing an electrical lead having a surrounding electrical screen and connecting said lead to said conductor, inserting a length of wire or other strip element into said tube at the end remote from said member, inserting said closure plug into said tube at the end remote from said glass member and moving the closure plug along the tube to the proximity of said glass member so that the conductor is in contact with the electrolyte, said wire extending between the plug and the wall of the glass tube and deforming the wall of the plug to form a groove therein which permits escape of air from said glass member, and withdrawing the wire from between the closure plug and the wall of the tube.

An embodiment of the invention will now be described, by way of example, with reference to the accompanying drawing, in which:

FIG. 1 is an elevation view of an electrode assembly manufactured in accordance with the method of the present invention.

FIG. 2 is a sectional view of the lower end of the glass tube of the assembly fitted with the membrane and containing the electrolyte, the closure plug and the electrode conductor, and FIG. 3 illustrates the components of the electrode assembly at one stage in the manufacture of the assembly.

Referring to FIGS. 1 and 2, the electrode assembly comprises an outermost cylindrical glass tube 1 which at its lower end at 2 is sealed to a glass member 3 at least part of which is formed as a thin glass membrane. The sealing of the tube to the member 3 results in a slight reduction of diameter as shown. The chamber formed by the lower end of the tube and the member 3 contains electrolyte 4, and an electrode conductor 5 has its lower end immersed in the electrolyte.

The electrode conductor 5 is in the form of a wire which is embedded in and extends through a closure plug 6 made of inert resilient electrical-insulating material, such as silicone rubber. The plug 6 has a cylindrical outer wall of a diameter slightly larger than the internal diameter of the glass tube 1 so that it is compressed when in position in the glass tube and is thus a tight sealing fit around its full periphery against the inside wall of the tube 1. The lower end of the plug 6 is conical to facilitate insertion of the plug into the top open end of the glass tube. The upper end of the plug 6 is of reduced diameter and fits within the lower end of an inner tube or sleeve 7, which can be of any suitable material, preferably of nylon, though it can be of polypropylene, or other similar material. The upper end of the plug 6 also has a central recess 8 which receives the end of a cable 9. The cable 9 is of the coaxial screened type, comprising an innermost central conductor 10, an insulator 11, a braided or laid electric conductive screening sheath 12 and an outer impervious insulating layer 13. The electrode conductor 5 passes through the plug 6 into the central recess 8 and is soldered or otherwise connected at 14 to the central conductor 10 of the cable. The screening sheath 12 of the cable and the outer insulating layer 13 are stripped back a short distance from the junction point 14 with the electrode conductor wire, as shown, and the end of the cable is sealed within the recess 8 by an inserted sealing material 15. This material should be flexible, and is conveniently an RTV sealant which is identified commercially as room temperature vulcanising (R.T.V.) sealant though other rubber based or rubber like sealants can be used.

At the upper end of the sleeve 7 the cable 9 passes through a further locating plug 16 fitting within the upper end of the tube 7. The plug 16 is formed with a head as at 17 which is a sealing fit within the outer tube 1. Alternatively the zone at 16 can be filled with a suitable resilient sealing means, such as R.T.V. The upper end of the assembly is covered and protected by a cap 18. The cap can be of plastics material, or of metal such as anodised aluminium and is preferably a friction fit on the tube 1. The cap may be sealed to or fixed to the tube, for example by adhesive. The end of the cable 9 carries a connecting plug 19.

In the assembly of the electrode the glass tube 1 is mounted in an upright position and the electrolyte liquid fed into the bottom of the tube 1. It is essential that none of the electrolyte comes into contact with the wall of the tube at the part thereof occupied by the plug 6 in the assembled electrode since this would form an electric track past the plug. For this reason the electrolyte is preferably inserted in the tube by a syringe having an outlet nozzle which extends to the bottom of the tube.

The cap 18, the locating plug 16, 17, and the sleeve 7 are then threaded in succession onto the cable 9, the central conductor 10 soldered to the electrode conductor 5 and the recess filled with the sealing material 15. The plug 6 together with the cable 9 is then ready for insertion in the glass tube 1.

It is however not possible merely to insert the plug 6 into the open end of the tube and then force the plug down the tube, for the reason that the closure plug is a sealing fit against the inside wall of the tube 1 and the air in the tube would be compressed, and if the plug was forced down to the position shown in FIG. 2 the pressure of air would either fracture the thin glass membrane at the bottom of the tube or tend to force the plug back up towards the top of the glass tube. It is a feature of the present invention that, prior to or simultaneously with insertion of the closure plug 6 into the glass tube 1, a thin wire 20 is inserted into the glass tube 1 through the open upper end thereof, as shown in FIG. 3. The plug 6, together with the sleeve 7 and cable 9, can then be moved downwards inside the tube 1 to the position shown in FIG. 2. The wire 20 extends between the plug and the wall of the glass tube and deforms the wall of the plug to form a groove 21 therein. The wall of the plug, even though it is compressed by the wall of the tube, does not completely fill the junction between the wire 20 and the wall of the tube 1 so that clearance passages are formed alongside the wire through which the air in the tube can escape past the plug when the plug is moved downwards to the position shown in FIG. 2. The wire 20 may be anchored to the top of the tube during the insertion of the plug 6, or alternatively the wire can be positioned alongside the plug and the wire and plug fed simultaneously into and down the tube. It is however essential that the wire 20 should not dip into the electrolyte since, in this event, when it was withdrawn the wire would smear electrolyte between the plug and the wall of the tube and form a track for electric current.

When the plug 6 is in the desired position in the tube 1, the wire 20 is withdrawn and the top of the tube sealed by the plug 16, 17 and cap 18. Upon withdrawal of the wire 20, the plug 6 expands into the space previously occupied by the wire and thereby provides an electrically insulating barrier between the electrolyte and the screening sheath 12 on the cable.

I claim:

1. An electrochemical electrode assembly comprising a tube of glass terminating in a glass member defining a glass membrane, said member containing a quantity of electrolyte in contact with the internal surface of said membrane, the external surface of said membrane being externally accessible, closure means retaining the electrolyte in said tube, an electrical conductor passing through said closure means and extending into said electrolyte, an electrical lead extending into said tube and connected to said conductor, an electrical screen surrounding said lead and extending to the proximity of said closure member, and a sleeve mounted within said tube and abutting at one end against said closure means, said closure means comprising a plug of resilient electrically-insulating material having two portions of different diameter, the larger diameter portion of said plug being of a size such that it is compressed by said tube and provides a sealing fit against the inside wall of said tube and said electrical conductor, and the smaller diameter portion of said plug being fitted within said sleeve and providing a sealing fit against the inside wall of the sleeve, whereby said plug forms an electrically-insulating barrier between the electrolyte and said electrical screen.

2. An electrochemical electrode comprising a tube of glass terminating in a glass member defining a glass membrane, said member containing a quantity of electrolyte in contact with the internal surface of said membrane, the external surface of said membrane being externally accessible, closure means retaining the electrolyte in said tube, a metallic electrical conductor passing through said closure means and extending into said electrolyte, and a co-axial screened electrical cable extending into said tube, said cable comprising an inner electrical lead connected to said conductor, a co-axial electrical screen surrounding said lead and insulated therefrom, and an external electrically insulating covering on said screen, characterized in that said closure means comprises a preformed plug of resilient electrical insulating material which in an unstressed condition has a transverse cross section of the same shape but larger diameter than the cross section of the interior of the tube, whereby upon insertion in the tube the plug is compressed by said tube between the wall of the tube and the electrical conductor, and the end of said cable is embedded in a mass of resilient electrically insulating sealing material on the adjacent end of the plug, whereby said plug and said mass of sealing material form an electrically insulating barrier between the electrolyte and the screen on the cable in direct sealing contact with said conductor, screen and tube.

3. An electrochemical electrode as claimed in claim 2, characterized in that the end of the plug remote from the electrolyte is formed with a recess, the end of the cable extends into said recess, and the mass of sealing material is cast in said recess so as to embed the end of the cable in the sealing material.

* * * * *